United States Patent [19]

Nablo

[11] Patent Number: 4,652,763
[45] Date of Patent: Mar. 24, 1987

[54] ELECTRON-BEAM IRRADIATION STERILIZATION PROCESS

[75] Inventor: Samuel V. Nablo, Lexington, Mass.

[73] Assignee: Energy Sciences, Inc., Woburn, Mass.

[21] Appl. No.: 717,328

[22] Filed: Mar. 29, 1985

[51] Int. Cl.⁴ .................................................. B65B 55/08
[52] U.S. Cl. ............................... 250/492.3; 250/492.1
[58] Field of Search ........................... 250/492.3, 492.1

[56] References Cited

U.S. PATENT DOCUMENTS

| | | | |
|---|---|---|---|
| 3,440,466 | 4/1969 | Colvin et al. | 313/35 |
| 3,702,412 | 11/1972 | Quintal | 313/299 |
| 3,780,308 | 12/1973 | Nablo | 250/492 |

Primary Examiner—Bruce C. Anderson
Assistant Examiner—Jack I. Berman
Attorney, Agent, or Firm—Rines and Rines, Shapiro and Shapiro

[57] ABSTRACT

A process for controlling the penetration of electron beam radiation through package coverings of products to insure sterilization of the covering wraps, but protecting the internal products and medium from electron beam penetration and x-ray generation and the like, as required for such applications as pharmaceutics, medicaments, parenteral drugs and devices, prostheses, food packaging and similar systems.

6 Claims, 9 Drawing Figures

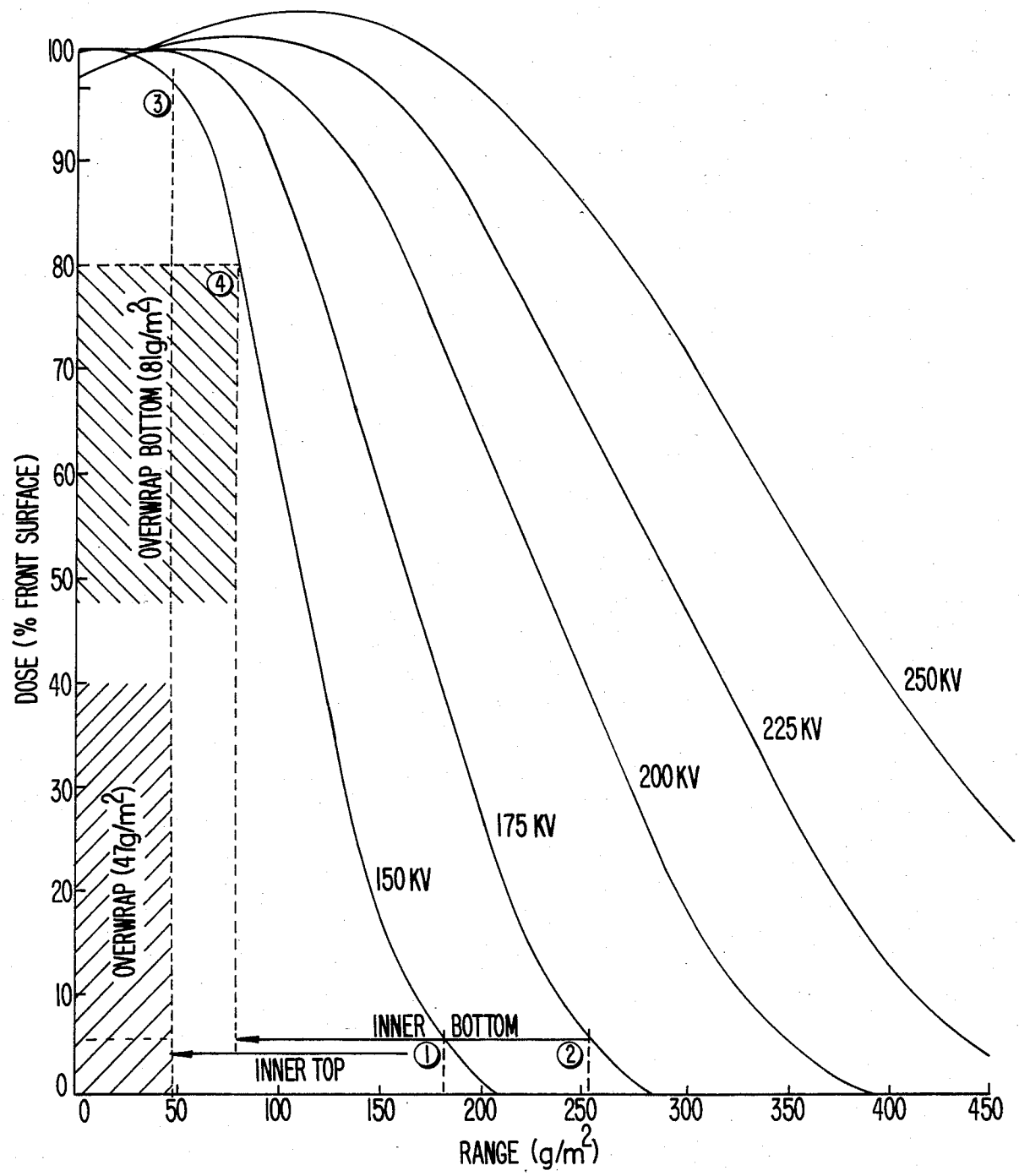

ELECTRON-BEAM IRRADIATION STERILIZATION PROCESS

The present invention relates to electron-beam irradiation processes for sterilization of materials and the like, being more particularly concerned with the selective sterilization of package wraps or coverings or lids or seals without penetration into interior media or products within the covering.

All of the standard techniques for the sterilization of materials used in the food packaging, surgical and medical products, pharmaceuticals and parenterals industries, are selected for their ability to penetrate "through" bulk material. High temperature autoclaves, for example, as widely used in the sterile or aseptic food packaging industry or medical products field, are applied in a manner such that a "time at temperature" can be realized in the most difficult to heat region of the product, such that no microorganisms, such as health prejudicing pathogens, can survive the bulk treatment, (in a two or three piece tin can, for example). Similarly, gases such as ethylene oxide (ETO) or hydrogen peroxide ($H_2O_2$) are applied to products in a manner such that the exposure time is adequate to ensure permeation of the product by the gas such that the deepest or most occluded region in the product is exposed to the sterilizing vapor for an adequate period of time to accomplish destruction of the pathogens and other microorganisms of concern. Where ionizing radiation such as gamma-rays, x-rays (such as those generated in the form of Bremsstrahlung from an electron accelerator) or energetic electrons themselves are used for bulk sterilization, the photon or electron energy is chosen so that the sterilization energy is transmitted to the deepest part of the product (measured in $gm/m^2$ or equivalent units of product depth) so that adequate energy is absorbed at these depths to eliminate the pathogens of concern.

As an example, for gamma radiation, the absorption of energy in the product is predicted by the well known experimental relation $I = I_o e^{-\mu d}$ where I is the radiation intensity reaching the depth d ($gm/m^2$) of the product, with original front surface intensity $I_o$, where $\mu$ is the mass absorption coefficient of the product being treated in units of $m^2/gm$. With the use of $Co^{60}$ gamma-rays, often used for gamma sterilization, the emitted gamma rays possess energies of 1.17 and 1.33 MeV as each radioactive $Co^{60}$ nucleus decays to its ground state of $Ni^{60}$. The average mass absorption coefficient in carbon, for example, of these gamma rays (of average energy 1.25 MeV) is 0.06 $cm^2/g$, so that the 90% absorption depth in carbon, for example, is that value of d for which $I/I_o = e^{-.06d} = 0.1$ or $d = 2.3/0.06 = 38.3$ $g/cm^2$. Hence a "uniform" treatment of 38.3 $g/cm^2$ or of 19 cm of carbon ($\rho = 2$ $g/cm^3$) could be achieved through bilateral irradiation of the product so that the gamma rays penetrate the product from both sides. Similar calculations may be used for x-rays or electrons using standard tables available in the literature.

The user of these ionizing radiation, gas or thermal energy sources must then calculate requisite "exposure" time for the product to the sterilizing technique being applied in order to provide the sterility assurance level, (SAL) required by the product. Techniques for the determination of these SAL's for ionizing radiation have been available in the literature for some time and for medical products referred to as the AAMI (Association for the Advancement of Medical Instrumentation) guidelines for application of the process. Basic sterilization requirements for medical products and medicaments are specified in the U.S. Pharmacopaiae.

There are a number of types of products, however, where it is decidedly not desirable to have the product subjected to the sterilizing agent. These may fall into a variety of categories, among which are:

(1) Pharmaceutical products such as opthalmological solutions, protein rich materials and heat or radiation sensitive products which have been manufactured under aseptic conditions but whose wrappers or containers must be sterilized for distribution and storage purposes after they are in a filled condition.

(2) Surgical and pharmaceutical products which are double wrapped in barrier, hermetically sealed pouches, so that the sterile inner pouch can be opened in a sterile field such as a Mayo tray (in the operating theater), awaiting the final opening of the inner pouch for use in the operating procedure. If the inner pouch is not opened, the product is often recycled for reasons of economy by rewrapping and resterilization. If the inner product is sensitive to or is degraded by the sterilization process, whatever that may be, it becomes desirable to apply a sterilization process whose depth of effect or penetration is limited to both surfaces of the outer pack and the outer surface of the inner pack. Products which fall into this category are surgical sutures or gut, solution loaded syringes, artificial skin, arterial or venous implants, impregnated or dry gauze pads, certain types of prostheses, and some types of more expensive disposable polymeric devices used in surgical procedure such as precharged catheters, ligation tubing, etc.

(3) Encapsulated products such as slow release pharmaceuticals, prescription drugs, vitamin products, etc. for which the manufacturer wishes to sterilize the outer capsule, which may be 0.5 mm or less in thickness ($<500$ $g/m^2$), without affecting the contents of the capsule. This procedure may also be accomplished through an outer barrier package which may be in the form of a pouch, blister pack, single portion packaging, etc.

(4) Sterile products in a primary barrier container which may later be compromised for purposes of metering the contents out, or for direct access to the product. Such a container could be a flexible pouch or tube (as for ointments, for example) in which a screw cap penetrates the sealed primary barrier. Or it can take the form of a rigid, capped container (plastic, glass or metal) in which the screw-applied or mechanically actuated penetration device permits metering of the contents under sterile conditions. This could take the form of a penetrating nipple or spout, for example, or a hermetically sealed conventional tear top on a rigid container. In all cases cited, the intent of the sterilization procedure is to sanitize or sterilize the field immediately exposed to the opened container through a protective barrier shroud so that the protective shroud and outer protected container surface are bathed in the sterilizing energy without penetration through the primary container wall so that the sensitive contents to be released from that container are in any way affected—particularly where physical or chemical degradation of the product could result.

(5) Repackaging applications where a manufacturer has decided to convert from paper packaged products using gas sterilization (in which materials like Tyvek ® are used), to a more robust film/foil barrier packaging construction. Here, the product may be already gas sterilized and the manufacturer does not wish to re-treat the product in the repackaging procedure.

(6) Product packaging in which the contents are gas sterilized out of the final package, are suitably outgassed and aerated under sterile conditions before packaging in the final barrier package. This can now be performed under aseptic conditions with sterile packaging material (such as a laminated film:foil:paper construction) or the gas or chemically sterilized product can be handled so that the barrier material is sterilized after product packaging with minimal effects of this sterilizing agent on the sterile product. The advantage of this "hybrid" technique is obvious to those skilled in the art of gas sterilization where the problems of gas introduction (via porous wicks, for example, or through Tyvek wrappers) cause long cycle times, while the problems of residual toxic residues such as chlorhydrine or active oxiding agents, usually necessitate time consuming and often expensive decontamination procedures, and the use of costly packaging materials and product handling procedures.

While we have previously developed surface and limited penetration electron-beam sterilization processes, as in U.S. Letters Pat. No. 3,780,308, these were concerned with the sterilizing of an exposed surface only and lacked control of opposite surface sterilization and further refined dose controls which are required for the above special applications. The process underlying the present invention, on the other hand, for these special and like applications utilizes the efficient lethality of energetic electrons for the sterilization application with a novel controlled depth of application and sterilization effect at desired depths, while minimizing the energy available for the production of x-rays which may deleteriously affect products at considerable depth.

An object of the present invention, accordingly, is to provide a novel electron beam irradiation process that is particularly adapted for sterilizing wrappings or other product packaging or coverings with controlled depth effect which protect the interior medium and product from direct electron beam penetration and indirect by-product x-ray or other radiation generation.

Other and further objects will be explained hereinafter and are more particularly delineated in the appended claims.

In summary, from one of its viewpoints, the invention embraces a process for the electron-beam irradiation sterilization of package coverings for products that are to be protected from such irradiation and x-ray and other by-product radiation normally indirectly generated by the same, that comprises, directing energetic electron beam radiation of substantially single energy spectral quality greater than 100 kilovolts but less than 300 kilovolts upon the outer surface of a covering enclosing an interior product and medium which are to be protected from direct and indirect radiation effects of the said beam; adjusting the value of the said beam with respect to the dimensions and electron absorption properties of the covering to optimize the deposition of energy from said beam at the preferred depth of the covering while minimizing both the deposition of such electron energy in strata at the covering-product and covering-medium interface and the indirect generation in said product and medium of x-ray and other by-product radiation during the process of the electron absorption within the covering; said adjusting comprising operating at a region of the depth:dose curve for the covering at which sterilization is effected at the inner covering surface with full electron beam penetration of the covering, but with the electron beam voltage adjusted below that at which direct electron and indirect x-ray radiation penetrate the adjacent strata of said medium and product. Preferred and best mode embodiments and details follow.

The invention will now be described in connection with the accompanying drawings, FIGS. 1(a) and 1(b) of which are ray diagrams illustrating electron beam scatter depth-dose characteristics;

FIGS. 4, 5 and 7 are graphs respectively illustrating depth-dose profiles, overwrap and innerwrap surface dose ratios as a function of voltage, and depth-dose profiles for glass syringe coverings.

Figure 1A:
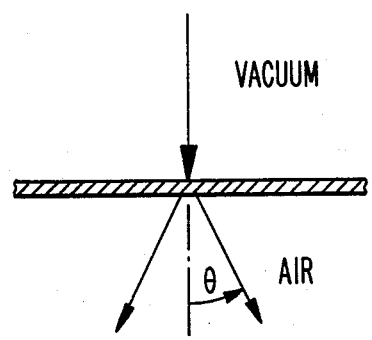

For practical electron beam sterilizers, the product treatment must be conducted under ambient pressure, so that the accelerated electrons must traverse an electron permeable window which can maintain a good vacuum in the sterilizer (accelerator) tube. Such windows or foils introduce a scattered distribution in the emergent electrons which where the scatter angle $\theta$ varies inversely with energy, directly with final thickness and atomic number, and the distribution generally possesses a gaussian shape. Of course, this process continues in air by multiple scattering shown schematically in FIG. 1(a).

Figure 1B:
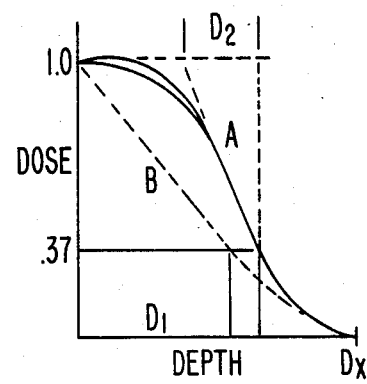

The absorption of the air/window scattered electrons in the target takes place again by multiple scattering with an energy absorption profile of the general characteristic shown in curve A of FIG. 1(b). If the mean scatter angle $\theta$ is excessive, or the energy variation in the beam is high due to voltage ripple, the absorption profile will degrade to a characteristic, more like curve B of FIG. 1(b). Such absorption curves are characterized by an end point range $D_x$ (often called the extrapolated range) determined by the accelerating voltage to which the electrons are subjected. The depth dose profile can be characterized by an "e folding" thickness in the product. If this 1/e (0.37) range is large as shown for $D_1$ for curve B, which is $>50\%$ of $D_x$, then the spectrum from which it was derived would be considered of degraded quality; i.e. excessive window thickness, air flight path to the product, large voltage ripple, etc. If the "e folding" range $D_2$ characteristic of the depth-:dose profile is small, compared with $D_x$ ($<40\%$ for example), then the spectrum would be considered of good quality for the type of application herein employed.

Figure 2:
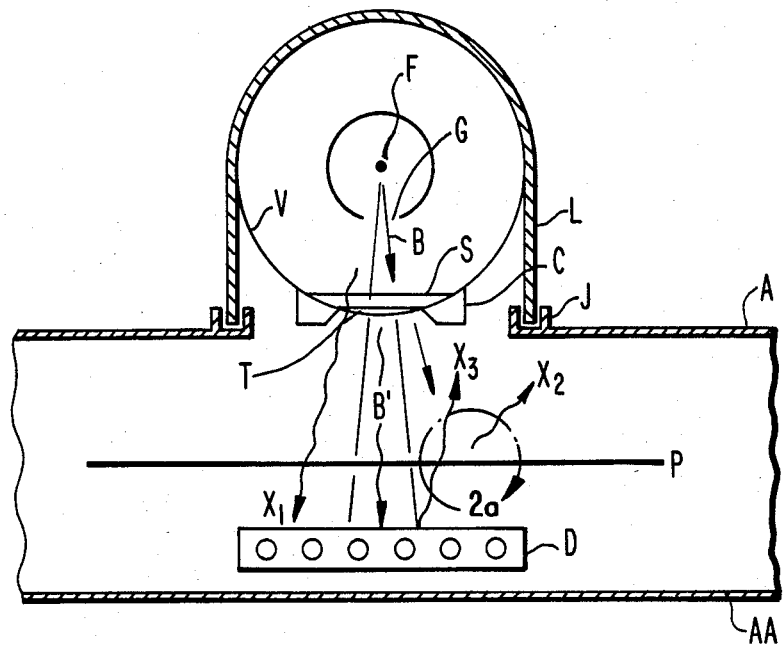
FIG. 2 is a longitudinal section of a preferred electron beam irradiation.
Figure 2A:
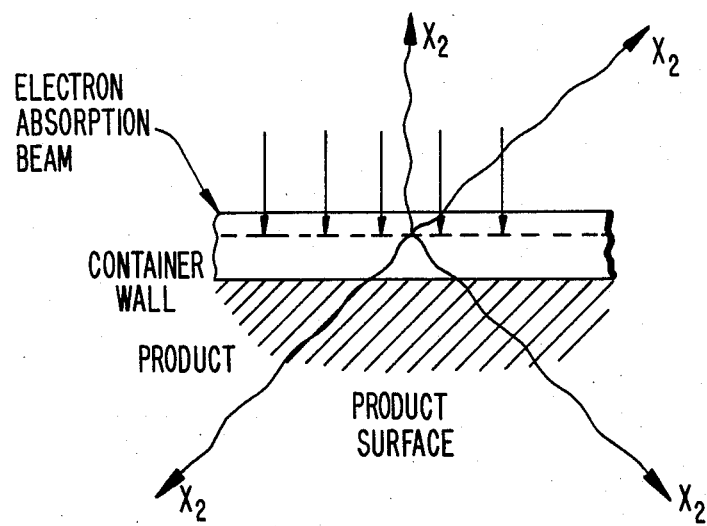
FIG. 2a is an exploded view of a portion of the product under treatment.

Electron beam machinery designed for substantially single energy good quality spectral performance has been described, for example, in U.S. Letters Pat. Nos. 3,780,308 and 3,702,412 of common assignee herewith, and which depend upon thin, supported and cooled window geometries as of the type described in U.S. Letters Pat. No. 3,440,466, for example. A schematic of such a sterilizer is shown in FIG. 2 in which electrons from source F in vacuum chamber V emerge from grid G and are accelerated across the vacuum gap to window foil T supported on cooled frame S of high transparency. Electron beam B in the vacuum tube generates x-rays (bremsstrahlung) in T and S as it passes out into air as scattered beam B'. As the sterilizing flux from B' stops in product P (expanded in FIG. 2a) it generates further x-rays $X_2$; while those electrons which stop in water-cooled collector D generate further x-rays $X_3$. The sterilizer is selfshielded via lead sheath L which mates with product handling tunnel A/AA at joints J so that it can be readily adapted to in-line use. It has been found preferable to restrict the generated primary electron energy variations to less than about ±2% through the window T of scattering half angles less than about 30°. In order to optimize the surface dose in product P to be sterilized, the electron beam energy must be matched to the penetration required to reach P (which may require penetration of an overwrap covering). In order to minimize the penetrating x-ray delivered dose, the sterilizer must be designed to minimize x-ray sources $X_1$ and $X_3$ and must be operated so as to minimize $X_2$.

EXAMPLES OF APPLICATION OF THE INVENTION

Figure 3:
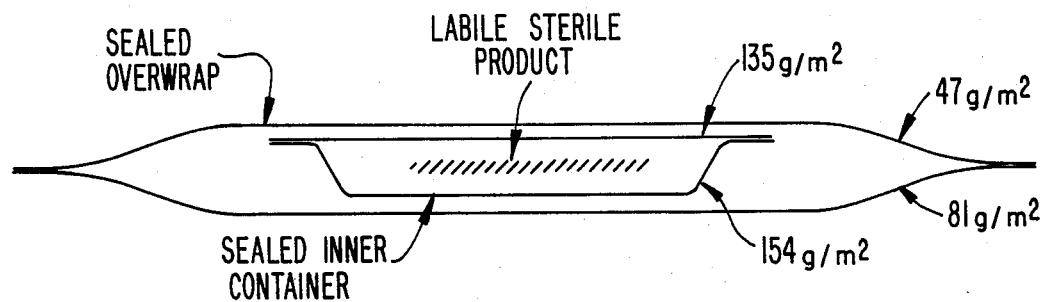
FIG. 3 is a section of a wrapped or covered sterile product with which the invention is usefully employed.

Consider, as an illustration, the use of the process of the invention for the sterilization of a double wrapped surgical suture, known to be quite sensitive to repetitive treatments by ionizing radiation or heat. First involved was the determination of the voltage appropriate for the product:outer dose ratios required for multiple re-sterilization. The product packaging construction was as shown in FIG. 3. The innerwrap foil top was made up of a functional coating, a polyester film laminated to aluminum foil and a vinyl inner coating. The total thickness of this 5-layer top covering was 135 g/m². The box or inner container to which it was sealed was of similar construction and 154 g/m² thick. The top member of the product overwrap was made up of 11 gm/m² of polypropylene, 1 g/m² of adhesive and 34 g/m² of Surlyn ® for a total thickness of 47 g/m² of Kraft paper, 16 g/m² of pp, 21 g/m² of foil and 1 g/m² of coating. The purpose of the application was to demonstrate the ability to deliver a 2.5 megarad dose to the outer surface of the inner package while fully sterilizing the overwrap covering, and with no penetration of the energy to the product contained in the inner container or "box".

Figure 5:
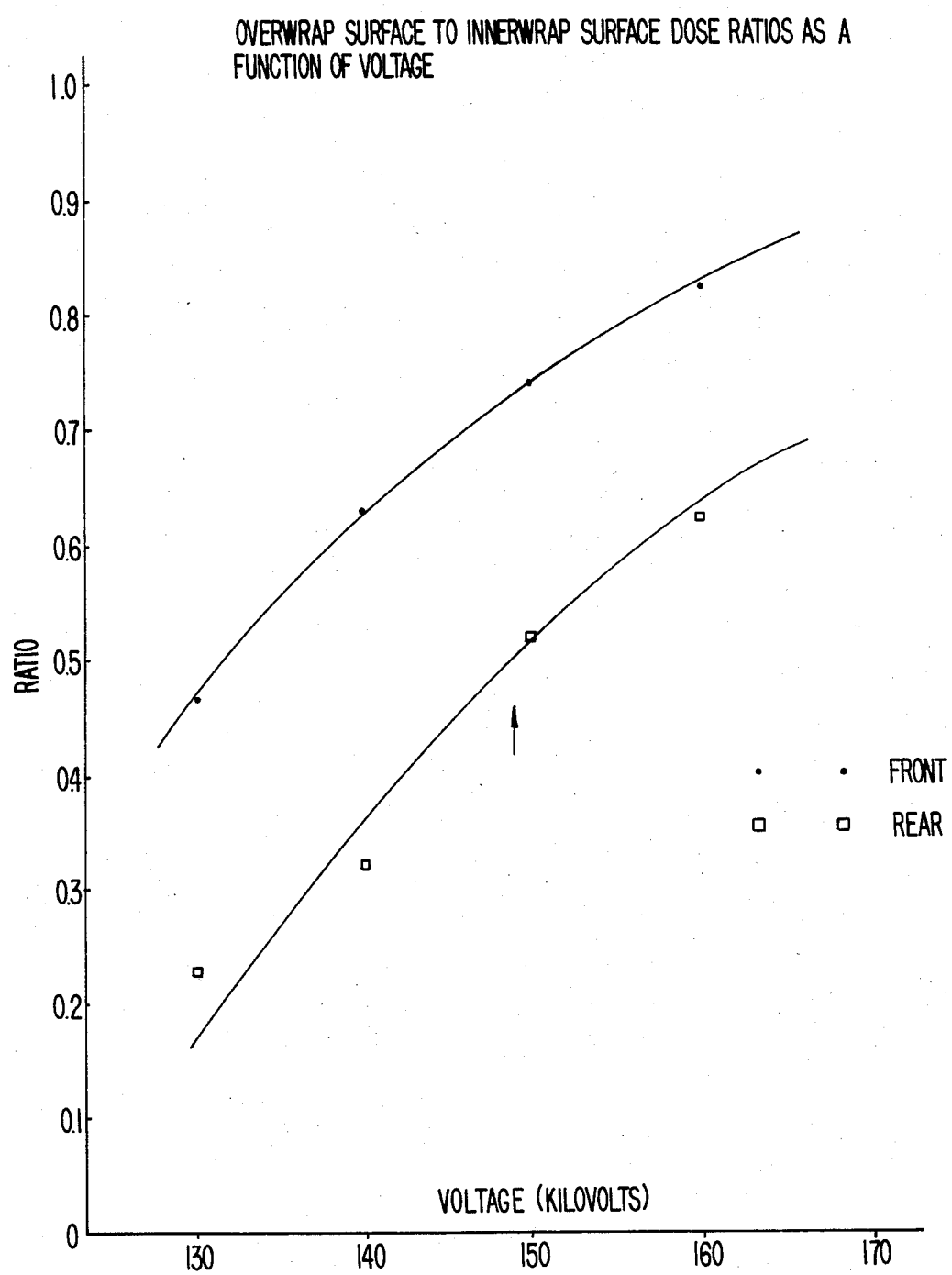

FIG. 4 shows the experimental depth:dose curves recorded for this type of electron sterilizer at increasing operating voltages, while the thicknesses of the four different package members are shown in the figure. The results for bilateral treatment are plotted in FIG. 5 and recorded in Table 1, below, as measured with dyed nylon dosimetry of the type manufactured by Far West Technology of Goleta, CA (FW-60) and calibrated at the National Bureau of Standards, Washington, DC. As shown in the table, no measurable leakage (penetration) to the inner product occurred until voltages of 160 kV were used. This includes both direct electron and x-ray delivered dose, as the dosimeters have a uniformly linear response to both forms of ionizing radiation. A minimum dose of 2.5 megarads on the outer surface of the inner package was obtained with no penetration to the product or medium surrounding the same.

TABLE 1

| Experimental Dosimetry for Package of FIG. 3 (Doses in Megarads) | | | | |
|---|---|---|---|---|
| Location | 130 kV | 140 kV | 150 kV | 160 kV |
| Top: Overwrap | 2.07 | 2.73 | 3.09 | 3.14 |
| Top: Innerwrap | 0.97 | 1.73 | 2.28 | 2.57 |
| Interior: Innerwrap - Upper | 0 | 0 | 0 | 0.08 |

TABLE 1-continued

| Experimental Dosimetry for Package of FIG. 3 (Doses in Megarads) | | | | |
|---|---|---|---|---|
| Location | 130 kV | 140 kV | 150 kV | 160 kV |
| Interior: Innerwrap - Lower | 0 | 0 | 0 | 0.02 |
| Bottom: Innerwrap | 0.50 | 0.96 | 1.54 | 1.94 |
| Bottom: Overwrap | 2.15 | 2.76 | 2.99 | 3.13 |

For this construction one could choose a bilateral treatment at, say, 150 kV and deliver overwrap:inner surface dose ratios of 0.74 and 0.52 to the top and bottom, respectively. For example, if a minimum dose of 2.5 megarads was desired on the inner box surface, the overwrap surface dose would be 3.38 and 4.81 megarads respectively. On the other hand, an elevation of the operating voltage on the "bottom" sterilizer could be used to reduce the overwrap surface dose, if desired. Since these doses (3–5 megarads) are well below those required to show any type of physical property degradation in film:foil:paper packaging construction of the type commonly used in sterile product packaging, a common operating voltage for bilateral sterilizers of this type would be used as a further simplification of sterilizer design and control.

Figure 6:
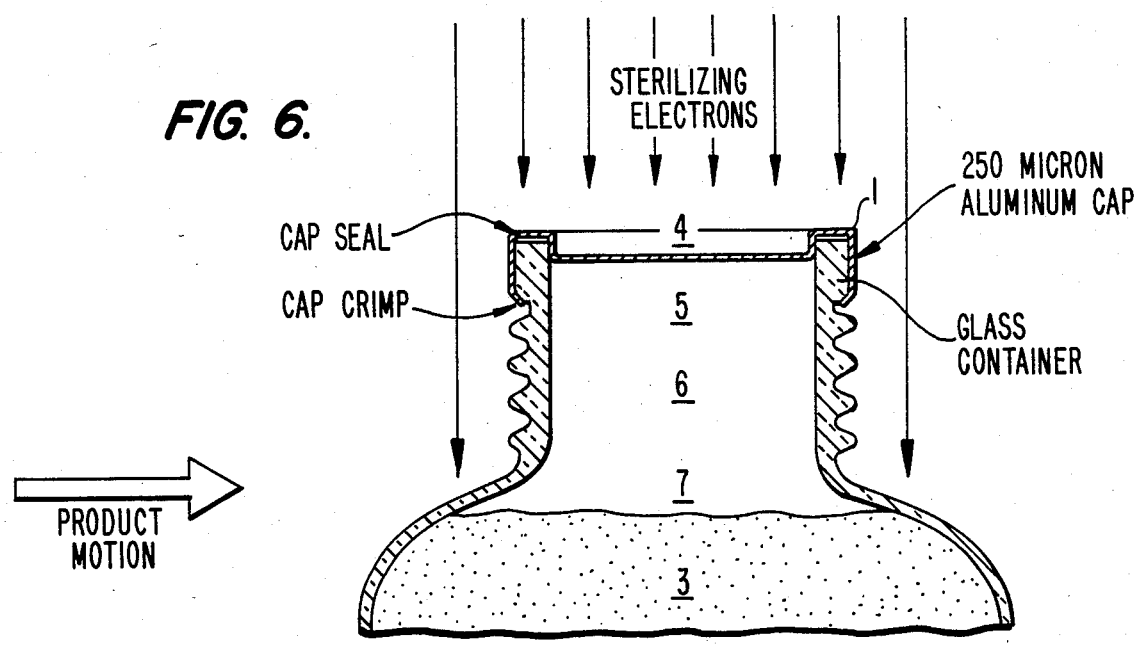
FIG. 6 illustrates application to a bottle or food container.

A second example of the application of this invention involves a packaged food product in which it was desired to maintain the dose received by the product/consumable to a level well below the 1000 rads specified in the U.S. Code of Federal Regulations, Title 21, as the maximum radiation dose which may be delivered to parenterals in the normal course of packaging (inspection). This is to be achieved while a dose of 3.5 megarads (capable of achieving a $10^{-7}$ letnality level with, say, a microorganism demonstrating a $D_{10}$ level of 0.5 megarads) is delivered over the outer surface of the capped bottle in which the product is packaged. Since the "thinnest" part of this particular package construction was the 250 micron aluminum cap over the glass bottle mouth, comparative dosimetry was performed about this region. The geometry is shown in FIG. 6 in which the puncturable cap 1 of thickness 250 microns is to be sterilized at 3.5 megarads on the bottle while product 3 is separated from the cap 1 plane by a headspace of 2 cm thickness. In order to determine experimentally the relative radiation levels 6 and 7 respectively, the following dosimetry was used. At location 4, packaged calibrated thin film dosimeters were used. At locations 5-7 LiF thermoluminescent dosimeters (TLD's) were used which possess excellent sensitivity and accuracy of measurement in the 0.001-100 rem region of interest in this study. In this application the 5-7 LiF thermoluminescent dosimeters (TLD's) were used to monitor photon (x-ray) irradiation alone, as the primary sterilizing electrons were unable to penetrate the aluminum cap or the bottle, so that the only ionizing radiation of concern in the interior of the package is that Bremsstrahlung generated by the primary beam as it stops in the container or cap. This process was therefore a demonstration of the ability to achieve high outer surface dose values with electrons while minimizing the interior dose delivered due to the x-rays which are concomitant with the electron stopping process. Since the photon production is known to vary as $V^{2.9}$ and roughly as $Z^2$ (where Z is the atomic number of the stopping material), the process is set up to maintain V minimum, depending upon the geometry of the product. For the food product of concern here, it was shown that with 3.5 megarads delivered to the cap surface by the electron sterilizer, the upper headspace dose was 42±5 rads, while the lower headspace dose under the same conditions was 32±6 rads, all recorded for an operating voltage of 200 kilovolts. These results illustrate the ability of the process to maintain a $3.5 \times 10^6:32$ dose ratio ($10^5:1$) across the 250 micron aluminum cap used in this product. Even higher ratios can be realized with lower operating voltages although the 32 rad dose measured at the upper surface of the product was already a factor of 30 under the maximum allowed dose of 1000 rads. Since the x-ray generation in and transmission of the $SiO_2$ glass wall of the bottle is considerably below that of the aluminum cap, it is clear that a continuous sterilizer in which the capped bottles move through the sterilizer zone (electron beam) will provide dose ratios of $10^5$ or more, if desired, permitting the cap surface:product dose ratios well above the $3.5 \times 10^6:10^3$ or $3.5 \times 10^3$ demanded for this application.

A third example of the beneficial use of the invention involves the surface of a glass syringe of the type employed for the packaging and administration of pharmaceuticals. The results described here were conducted with a Becton-Dickinson type SCF pre-filled syringe delivery system with a capacity of 2.25 ml. The wall thickness of this type of glass syringe is 1 mm so that this wall covering, in which the radiation sensitive or heat sensitive pharmaceutical is confined, is separated from the surface to be sterilized by some 2300 $g/m^2$ of material ($SiO_2$). As in the prior example, measurements were made to determine the actual ionizing radiation dose delivered to the inner volume of the syringe where the pharmaceutical or otherwise labile liquid would normally be located, when the syringe was sterilized with energetic electrons under otherwise normal conditions.

For the prepackaged geometry of interest here, the syringe itself was contained in a paper/polyethylene package with thicknesses of 200 $\mu$ (75 $g/m^2$) and 75 $\mu$ (75 $g/m^2$) respectively. Thin film dosimeters were placed on the surface of the syringe barrel during the irradiations in order to determine the electron delivered dose to the product surface. Lithium fluoride (LiF) thermoluminescent dosimeters provided and read out by R. S. Landauer Jr. & Co., were placed in the interior of the glass barrel of the syringe in order to give a precise measurement of the x-ray delivered dose. Irradiations were then performed at electron sterilizer voltages of 140, 160 and 180 kilovolts in order to study the role of the beam energy and its effect on the ratio of surface dose to the x-ray delivered dose deep in the product. In these measurements, various fractions of the electrons were stopping in the hydrocarbon package or in the silicon dioxide of the glass barrel covering depending upon their energies (depth of penetration). The values shown in Table 2 are based upon experimentally determined values. Data are also shown for a geometry in which a thick tantalum plate was used to provide back surface dose enhancement of the electron delivered dose to the product.

TABLE 2

| Dose Ratio Data as a Function of Sterilizer Voltage (Surface Dose:Internal Dose Ratio ($\times 10^5$)) | | | |
| --- | --- | --- | --- |
| Product | 140 kV | 160 kV | 180 kV |
| 2.25 ml Packaged Syringe on Steel Tray | 1.4 | 1.5 | 1.8 |
| 2.25 ml Packaged Syringe on Ta Backscatter Plate | 1.2 | 2.4 | 1.8 |
| 8.0 ml Packaged Syringe on Aluminum Tray | 1.5 | 3.0 | 2.5 |
| 8.0 ml Packaged Syringe on Ta Backscatter Plate | 1.7 | 2.4 | 2.4 |

The results show that for the 1 mm thick glass barrels characteristic of medical syringes, electron:x-ray dose ratios of $10^5:1$ are easily achieved using the technique of the present invention. That is to say, for a surface dose of 2.5 megarads delivered to the outer surface of the device, the x-ray dose delivered to the product contained in the device is 10 rads or less. It can be seen from the data of Table 2 that 140 kV was somewhat below the optimum treatment point as the electron energy was inadequate to give full penetration of the 75 $g/m^2$ outer wrap so that one could deliver a dose to the surface of the syringe comparable to the (surface) dose delivered to the outerwrap. On the other hand, 180 kV began to approach an excess energy where there was "overpenetration" of the outerwrap so that an excessive amount of electron energy was delivered to the syringe glass wall leading to increased bremsstrahlung generation (and hence a decrease in the electron (outer):x-ray (inner) dose ratio). This effect can be seen in a comparison of the ratios in the 160 and 180 kilovolt columns of the table. The inadequate energy effect is also pronounced in the second and third cases where one sees a doubling of the ratio in going from 140 to 160 kilovolts due to the increasing ability of the sterilizing beam to penetrate the overwrap.

Figure 7:
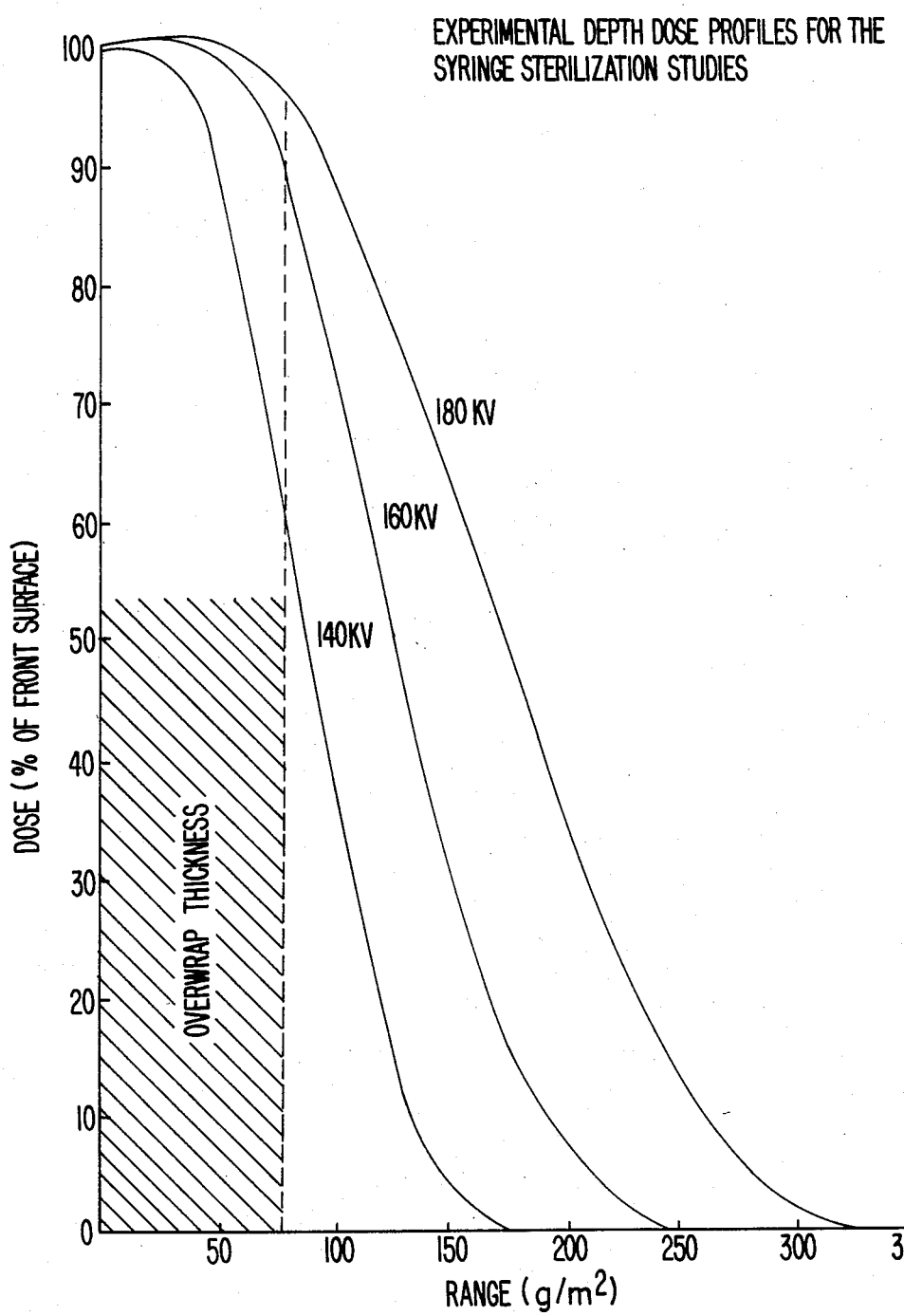

FIG. 7 shows this effect schematically using the experimentally determined depth:dose profiles for electrons delivered from the sterilizer at 140, 160 and 180 kilovolts under the same conditions as those used in the experiment reviewed in Table 1.

The 75 $g/m^2$ outerwrap covering is shown on the penetration curve and one sees that as the electron energy increases, increasing amounts of electron energy are delivered to the syringe wall—60% at 140 kV, 90% at 160kV and 100% at 180kV. Since these electrons are the primary source of x-rays delivered to the syringe inner volume, (a lesser flux of x-rays arises from electron generated bremsstrahlung in the window and window frame assembly of the sterilizer, or from electrons stopped in the tray itself), the electron:x-ray dose ratio decreases with increasing energy as soon as "full" overwrap penetration is possible—a result which is indeed shown from the experiment.

The process taught herein therefore requires a knowledge of the effective penetration characteristics of the sterilizing electron flux so that a suitable operating point is chosen such that adequate inner surface (overwrap:-product interface) illumination is achieved to accomplish sterilization, while minimizing the electron energy deposited in the product which serves as the primary source of bremsstrahlung or penetrating x-rays which can affect its physical properties.

The invention is also useful in disinfestation or pasteurization processes utilizing the same techniques, and, further, for curing or polymerization processes which utilize the same art as, for example, the surface crosslinking of a thick polyolefinic material, or the surface grafting of material to a radiation or thermolabile substrate. Disinfestation or pasteurization of foodstuffs can also be performed where the process is used to treat only the surface (or pericarp) of a product without penetration to the consumed inner portion (endocarp) of the product.

Further modifications will also occur to those skilled in this art, such being considered to fall within the spirit and scope of the invention as defined in the appended claims.

What is claimed is:

1. A process for the electron-beam irradiation sterilization of package coverings for products that are to be protected from such irradiation and x-ray and other by-product radiation normally indirectly generated by the same, that comprises, directing energetic electron beam radiation of substantially single energy spectral quality greater than 100 kilovolts but less than 300 kilovolts upon the outer surface of a covering enclosing an interior product and medium which are to be protected from direct and indirect radiation effects of the said beam; adjusting the value of the said beam with respect to the dimensions and electron absorption properties of the covering to optimize the deposition of energy from said beam at the preferred depth of the covering while minimizing both the deposition of such electron energy in strata at the covering-product and covering-medium interface and the indirect generation in said product and medium of x-ray and other by-product radiation during the process of the electron absorption within the covering; said adjusting comprising operating at a region of the depth:dose curve for the covering at which sterilization is effected at the inner covering surface with full electron beam penetration of the covering, but with the electron beam voltage adjusted below that at which direct electron and indirect x-ray radiation penetrate the adjacent strata of said medium and product.

2. A process as claimed in claim 1 and in which the electron beam dose external to the covering at its outer surface is of the order of 3 to 5 megarads, with adjustment such that at the inner surface of the covering a sterilizing dose of about 2.5 megarads is delivered.

3. A process as claimed in claim 1 and in which the product comprises glass, the electron beam voltage is adjusted to between 140 and 180 kilovolts, the covering is of the order of 75 gm/m$^2$ and the electron beam-to-x-ray delivered dose ratio is of the order of $10^5$:1.

4. A process as claimed in claim 1 and in which the said electron beam is generated with primary electron energy variations of less than about ±2% through an electron-beam permeable window of scattering half angles less than about 30°.

5. A process as claimed in claim 4 and in which the e-folding depths for the delivered electron beam are adjusted to less than about 40% of the extrapolated range of the sterilization electron flux.

6. A process as claimed in claim 1 and in which the package covering is constituted by providing a glass syringe the interior of which contains the said interior product to be protected from direct and indirect radiation.

* * * * *